United States Patent
Barton et al.

(10) Patent No.: US 6,905,849 B1
(45) Date of Patent: Jun. 14, 2005

(54) PROCESS FOR PREPARING CLAVAM DERIVATIVES BY USING POLYPEPTIDES HAVING β-LACTAM SYNTHETASE ACTIVITY

(75) Inventors: Barry Barton, Worthing (GB); Heather Jane McNaughton, Oxford (GB); Christopher Joseph Schofield, Oxford (GB); Jan Edward Thirkettle, Worthing (GB)

(73) Assignee: SmithKline Beecham plc, Brentford (GB)

( * ) Notice: Subject to any disclaimer, the term of this patent is extended or adjusted under 35 U.S.C. 154(b) by 0 days.

(21) Appl. No.: 09/743,209

(22) PCT Filed: Jul. 15, 1999

(86) PCT No.: PCT/GB99/02301

§ 371 (c)(1),
(2), (4) Date: Oct. 5, 2001

(87) PCT Pub. No.: WO00/03581

PCT Pub. Date: Jan. 27, 2000

(30) Foreign Application Priority Data

Jul. 17, 1998 (GB) .............................................. 9815666

(51) Int. Cl.⁷ ............................................... C12P 17/10
(52) U.S. Cl. ....................................................... 435/121
(58) Field of Search ......................................... 435/121

(56) References Cited

U.S. PATENT DOCUMENTS 6,232,106 B1 * 5/2001 Jensen et al. ................ 435/183
6,514,735 B1 * 2/2003 Jensen et al. ................ 435/191
6,589,775 B1 * 7/2003 Jensen et al. ........... 435/252.35

FOREIGN PATENT DOCUMENTS

| CA | 2108113 | 4/1995 |
| WO | WO 94/12654 | 6/1994 |

OTHER PUBLICATIONS

Jensen et al. Biosynthesis and molecular genetics of clavulanic acid. Antonie Van Leeuwenhoek (1999) (1–2): 125–133.*
Li et al. Expansion of the Clavulanic Acid Gene Cluster: Identification and In Vivo Functional Analysis of Three New Genes Required for Biosynthesis of Clavulanic Acid by *Streptomyce clavuligerus*. Journal of Bacteriology (2000) 182(14): 4087–4095.*
McNaughton, et al., "β–Lactam Synthetase: Implications for β–Lactamase Evolution". *Chem. Commun.*, 21: 2325–2326 (1998).
Bachmann, et al., "β–Lactam Synthetase: A New Biosynthetic Enzyme". *Proc. Natl. Acad. Sci. USA*, 95: 9082–9086 (1998).

* cited by examiner

Primary Examiner—Kathleen Kerr
(74) Attorney, Agent, or Firm—Andrea V. Lockenour; Jeffrey A. Sutton

(57) ABSTRACT

The present invention relates to a new process for the synthesis of clavam compounds, in particular clavulanic acid. In one aspect, the invention relates to *Streptomyces clavuligerus* β-lactam synthetase polypeptide sand *Streptomyces clavuligerus* β-lactam synthetase polynucleotides, recombinant materials thereof and methods for their production. In another aspect, the invention relates to methods for using such polypeptides and polynucleotides.

8 Claims, No Drawings

SEQUENCE LISTING

<160> NUMBER OF SEQ ID NOS: 6

<210> SEQ ID NO 1
<211> LENGTH: 1542
<212> TYPE: DNA
<213> ORGANISM: Streptomyces clavuligerus

<400> SEQUENCE: 1

```
atgggggcac cggttcttcc ggctgccttc gggttcctgg cctccgcccg aacgggcggg      60
ggccgggccc ccggcccggt cttcgcgacc cggggcagcc acaccgacat cgacacgccc     120
caggggagc gctcgctcgc ggcgaccctg gtgcacgccc cctcggtcgc gcccgaccgc      180
gcggtggcgc gctccctcac cggcgcgccc accaccgcgg tgctcgccgg tgagatctac     240
aaccgggacg aactcctctc cgtgctgccc gccggacccg cgccggaggg ggacgcggag     300
ctggtcctgc ggctgctgga acgctatgac ctgcatgcct ccggctggt gaacgggcgc      360
ttcgcgaccg tggtgcggac cggggaccgg gtcctgctcg ccaccgacca cgccggttcg     420
gtgccgctgt acacctgtgt ggcgccgggc gaggtccggg cgtccaccga ggccaaggcg     480
ctcgccgcgc accgcgaccc gaagggcttc ccgctcgcgg acgcccgccg ggtcgccggt     540
ctgaccggtg tctaccaggt gcccgcgggc gccgtgatgg acatcgacct cggctcgggc     600
accgccgtca cccaccgcac ctggaccccg ggcctctccc gccgcatcct gccggagggc     660
gaggccgtcg cggccgtgcg ggccgcgctg gagaaggccg tcgcccagcg ggtcaccccc     720
ggcgacaccc cgttggtggt gctctccggc ggaatcgact cctccggggt cgcggcctgt     780
gcgcaccggg cggccgggga actggacacg gtgtccatgg caccgacac gtccaacgag      840
ttccgcgagg cccgggcggt cgtcgaccat ctgcgcaccc ggcaccggga gatcaccatc     900
ccgaccaccg agctgctggc gcagctcccg tacgcggtgt gggcctccga gtcggtggac     960
ccggacatca tcgagtacct gctcccctg acagcgctct accgggcgct cgacgggccg    1020
gagcgccgca tcctcaccgg gtacggcgcg gacatccccc tcgggggcat gcaccgcgag    1080
gaccggctgc ccgcgctgga caccgttctc gcgcacgaca tggccacctt cgacgggctg    1140
aacgagatgt ccccggtgct gtccacgctg gcggggcact ggaccaccca cccgtactgg    1200
gaccgggagg tcctcgatct gctggtctcg ctggaggccg gctcaagcg gcggcacggc     1260
cgggacaagt gggtgctgcg cgccgcgatg gccgacgccc tcccggcgga gaccgtcaac    1320
cggcccaagc tgggcgtcca cgagggctcg ggcaccacgt cctcgttctc ccggctgctg    1380
ctggaccacg tgtcgccga ggaccgcgtc acgaggcga agcggcaggt ggtgcgcgag     1440
ctgttcgatc tcacggtcgg gggcggacgg caccctccg aggtggacac cgacgatgtg     1500
gtgcgctccg tggccgaccg gaccgcgcgg ggggcggcct ag                        1542
```

<210> SEQ ID NO 2
<211> LENGTH: 512
<212> TYPE: PRT
<213> ORGANISM: Streptomyces clavuligerus

<400> SEQUENCE: 2

```
Gly Ala Pro Val Leu Pro Ala Ala Phe Gly Phe Leu Ala Ser Ala Arg
 1               5                  10                  15

Thr Gly Gly Arg Ala Pro Gly Pro Val Phe Ala Thr Arg Gly Ser
            20                  25                  30

His Thr Asp Ile Asp Thr Pro Gln Gly Glu Arg Ser Leu Ala Ala Thr
```

```
                35                  40                  45
Leu Val His Ala Pro Ser Val Pro Asp Arg Ala Val Ala Arg Ser
 50                  55                  60

Leu Thr Gly Ala Pro Thr Thr Ala Val Leu Ala Gly Glu Ile Tyr Asn
 65                  70                  75                  80

Arg Asp Glu Leu Leu Ser Val Leu Pro Ala Gly Pro Ala Pro Glu Gly
                 85                  90                  95

Asp Ala Glu Leu Val Leu Arg Leu Leu Glu Arg Tyr Asp Leu His Ala
                100                 105                 110

Phe Arg Leu Val Asn Gly Arg Phe Ala Thr Val Val Arg Thr Gly Asp
                115                 120                 125

Arg Val Leu Leu Ala Thr Asp His Ala Gly Ser Val Pro Leu Tyr Thr
                130                 135                 140

Cys Val Ala Pro Gly Glu Val Arg Ala Ser Thr Glu Ala Lys Ala Leu
145                 150                 155                 160

Ala Ala His Arg Asp Pro Lys Gly Phe Pro Leu Ala Asp Ala Arg Arg
                165                 170                 175

Val Ala Gly Leu Thr Gly Val Tyr Gln Val Pro Ala Gly Ala Val Met
                180                 185                 190

Asp Ile Asp Leu Gly Ser Gly Thr Ala Val Thr His Arg Thr Trp Thr
                195                 200                 205

Pro Gly Leu Ser Arg Arg Ile Leu Pro Glu Gly Glu Ala Val Ala Ala
                210                 215                 220

Val Arg Ala Ala Leu Glu Lys Ala Val Ala Gln Arg Val Thr Pro Gly
225                 230                 235                 240

Asp Thr Pro Leu Val Val Leu Ser Gly Gly Ile Asp Ser Ser Gly Val
                245                 250                 255

Ala Ala Cys Ala His Arg Ala Ala Gly Glu Leu Asp Thr Val Ser Met
                260                 265                 270

Gly Thr Asp Thr Ser Asn Glu Phe Arg Glu Ala Arg Ala Val Val Asp
                275                 280                 285

His Leu Arg Thr Arg His Arg Glu Ile Thr Ile Pro Thr Thr Glu Leu
                290                 295                 300

Leu Ala Gln Leu Pro Tyr Ala Val Trp Ala Ser Glu Ser Val Asp Pro
305                 310                 315                 320

Asp Ile Ile Glu Tyr Leu Leu Pro Leu Thr Ala Leu Tyr Arg Ala Leu
                325                 330                 335

Asp Gly Pro Glu Arg Arg Ile Leu Thr Gly Tyr Gly Ala Asp Ile Pro
                340                 345                 350

Leu Gly Gly Met His Arg Glu Asp Arg Leu Pro Ala Leu Asp Thr Val
                355                 360                 365

Leu Ala His Asp Met Ala Thr Phe Asp Gly Leu Asn Glu Met Ser Pro
                370                 375                 380

Val Leu Ser Thr Leu Ala Gly His Trp Thr Thr His Pro Tyr Trp Asp
385                 390                 395                 400

Arg Glu Val Leu Asp Leu Leu Val Ser Leu Glu Ala Gly Leu Lys Arg
                405                 410                 415

Arg His Gly Arg Asp Lys Trp Val Leu Arg Ala Ala Met Ala Asp Ala
                420                 425                 430

Leu Pro Ala Glu Thr Val Asn Arg Pro Lys Leu Gly Val His Glu Gly
                435                 440                 445

Ser Gly Thr Thr Ser Ser Phe Ser Arg Leu Leu Leu Asp His Gly Val
450                 455                 460
```

```
Ala Glu Asp Arg Val His Glu Ala Lys Arg Gln Val Val Arg Glu Leu
465                 470                 475                 480

Phe Asp Leu Thr Val Gly Gly Arg His Pro Ser Glu Val Asp Thr
                485                 490                 495

Asp Asp Val Val Arg Ser Val Ala Asp Arg Thr Ala Arg Gly Ala Ala
            500                 505                 510

<210> SEQ ID NO 3
<211> LENGTH: 29
<212> TYPE: DNA
<213> ORGANISM: Artificial Sequence
<220> FEATURE:
<223> OTHER INFORMATION: PCR primer

<400> SEQUENCE: 3
ggaatcccat atgggggcac cggttcttc                               29

<210> SEQ ID NO 4
<211> LENGTH: 26
<212> TYPE: DNA
<213> ORGANISM: Artificial Sequence
<220> FEATURE:
<223> OTHER INFORMATION: PCR primer

<400> SEQUENCE: 4
cgcggattcc taggccgccc cccgcg                                  26

<210> SEQ ID NO 5
<211> LENGTH: 16
<212> TYPE: PRT
<213> ORGANISM: Artificial Sequence
<220> FEATURE:
<223> OTHER INFORMATION: orf3 protein

<400> SEQUENCE: 5

Val Gly Gly Gly Arg His Pro Ser Glu Val Asp Thr Asp Asp Val Cys
1               5                   10                  15

<210> SEQ ID NO 6
<211> LENGTH: 20
<212> TYPE: PRT
<213> ORGANISM: Artificial Sequence
<220> FEATURE:
<223> OTHER INFORMATION: orf3 protein

<400> SEQUENCE: 6

Gly Ala Pro Val Leu Pro Ala Ala Phe Gly Phe Leu Ala Ser Ala Arg
1               5                   10                  15

Thr Gly Gly Gly
            20
```

PROCESS FOR PREPARING CLAVAM DERIVATIVES BY USING POLYPEPTIDES HAVING β-LACTAM SYNTHETASE ACTIVITY

The present invention relates to a new process for the synthesis of clavam compounds, in particular clavulanic acid. In one aspect the invention relates to β-lactam synthetase polypeptides and β-lactam synthetase polynucleotides, recombinant materials thereof and methods for their production. In another aspect, the invention relates to methods for using such polypeptides and polynucleotides.

A common feature of all penicillins and cephalosporins is the presence of a β-lactam ring which is vital to their antibiotic activity. β-lactam compounds are susceptible to degradation by β-lactamase enzymes which are produced by several clinically important microorganisms. The ability of these microorganisms to produce β-lactamase activities is a major factor in the spread of antibiotic resistance among clinically relevent microorganisms.

Clavulanic acid, which also comprises a β-lactam ring, is a potent inhibitor of β-lactamases and has been used successfully in combination with β-lactam antibiotics in the treatment of infections caused by β-lactamase producing microorganisms. Clavulanic acid is Z-(2R,5R)3-(β-hydroxy-ethylidene)-7-oxo-4-oxa-1-azabicyclo[3.2.0]heptane-2 carboxylic acid.

An understanding of the biosynthesis of these β-lactam molecules is central to improvements in the manufacture of existing antibiotics, for example Augmentin (Trade Mark of SmithKline Beecham plc), and for designing novel antibacterial compounds. Although the biosynthetic pathways of penicillins and cephalosporins are well studied, much remains to be learned about the biosynthesis of clavulanic acid.

Several steps in the clavulanic acid biosynthetic pathway have been elucidated, predominantly those within the central part of the pathway, and in some cases their corresponding enzymatic activities have been identified. These enzymatic activities have been the subject of several publications and patent applications, for example EP 0349121 concerns clavaminate acid synthase, WO 95/03416 discloses the enzyme clavulanic acid dehydrogenase and WO 94/12654 the proclavaminate amidinohydrolase.

It has been shown that in *Streptomyces clavuligerus*. a clavulanic acid producing organism, the genes responsible for the biosynthesis of clavulanic acid are clustered together close to the gene cluster involved in the biosynyethesis of the penicillin and cephalosporin molecules which are also produced by this organism (Jensen, SE et al, 1993, Industrial Microorganisms, Basic and Applied Molecular Genetics, p169–176; American Society for Microbiology). The DNA sequence and predicted open reading frames for the clavulanic acid biosynthesis cluster are disclosed in Canadian patent application no. 2108113. This patent application discloses an 11.6 kb fragment which encompasses 8 open reading frames (orf2 to orf9), which, when introduced into a non-clavulanic acid producing *Streptomyces* strain, confers the ability to produce clavulanic acid. The functions of some of the proteins predicted to be encoded by these orfs have been deduced based on known activity (eg. orf 5 is known to encode clavaminate synthase II; Marsh et al , 1992, Biochem, 31 p12648–12657) or by similarity with known proteins (eg. orf2 shows a high level of homology with acetohydroxyacid synthase (Canadian patent application no. 2108113)). Some proteins, however, remain of unknown function.

The present invention is based on the finding that the orf3 gene encodes an enzyme that is alone capable of the conversion of the β-amino acid (formed from arginine and pyruvate) into the β-lactam form, early in the clavulanic acid biosynthesis pathway.

The polynucleotide sequence of orf3 is given in SEQ ID NO:1 and the polypeptide encoded by orf3 is given in SEQ ID NO:2; both sequences are disclosed in Canadian patent application no. 2108113.

Accordingly the present invention provides a process for preparing a β-lactam compound of formula (I) or salt thereof

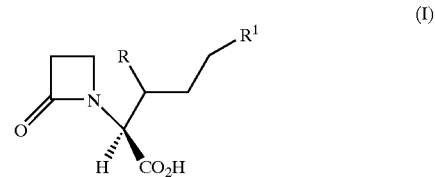

(I)

wherein R is H or OH and $R^1$ is

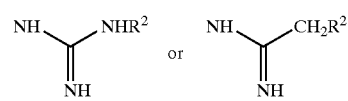

and where $R^2$=H or $C_{1-6}$ alkyl by contacting a β-amino acid compound of formula (II) or salt thereof

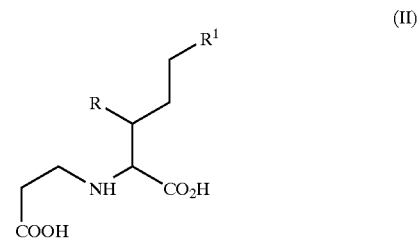

(II)

where the variables are as defined in formula (I) with a polypeptide having at least 95% identity to the amino acid sequence of SEQ ID NO:2, over the entire length of SEQ ID NO:2, and having β-lactam synthetase activity.

Compounds of formula (I) can be converted thereafter to clavulanic acid or other clavam compounds by conventional means. By 'other clavams' we mean compounds containing a 7-oxo-4-oxa-1-azabicyclo[3.2.0]heptane nucleus [J.C.S., Chem. Commun. (1979), 282].

In a further aspect the compound of formula (I), prepared in accordance with the process of the invention, is converted to other clavams and clavam derivatives by treatment with an enzyme system derived from *Streptomyces clavuligerus*.

In a preferred embodiment the process concerns contacting a β-amino acid compound of formula (III) with said polypeptide having β-lactam synthetase activity. The compound of formula (III) is $N^2$-(2-carboxyethyl)-(S)-arginine first disclosed in WO 9412654. Methods for the production of a compound of formula (III) are disclosed in WO 9412654.

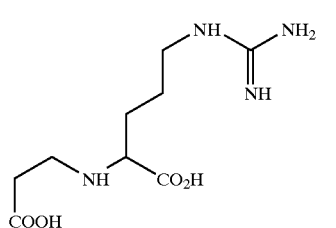

Contacting a compound of formula (III) with a polypeptide having β-lactam synthetase enzyme results in the closure of the β-lactam ring to give a β-lactam compound of formula (IV), which is (2S)-5-guanidino-2-(2-oxo-azetidin-1-yl) pentanoic acid.

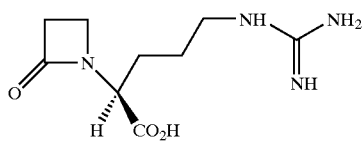

In a preferred aspect the compound of formula (IV), prepared in accordance with the process of the invention, is converted to clavulanic acid by treatment with an enzyme system derived from *Streptomyces clavuligerus*. The enzyme system includes the enzymes of the clavulanic acid biosynthetic pathway, for example clavaminic acid synthase (Baldwin, J E et al, J.Chem.Soc.,Chem.Commun. 500); proclavaminate amidinohydrolase (disclosed in WO 94/12654); clavulanic acid dehydrogenase (disclosed in WO 95/03416) or any one, or combinations of, the enzymes encoded by the clavulanic acid biosynthesis gene cluster disclosed in Canadian patent application no. 2108113.

Such enzymes may be provided in isolated form, in recombinant hosts transformed with cloned genes encoding the enzymes or by contact with *Streptomyces clavuligerus* whole cells.

The polypeptide having at least 95% identity with the amino acid sequence of SEQ ID NO:2 will herein be referred to as β-lactam synthetase. The β-lactam synthetase preferably has 97–99% identity with the amino acid sequence of SEQ ID NO:2. Such polypeptides include those comprising the amino acid sequence of SEQ ID NO:2. In a most preferred aspect the polypeptide has the amino acid sequence of SEQ ID NO:2.

Polypeptides useful in the present invention will possess the β-lactam synthetase activity. In one aspect, modified polypeptides may be employed which increase the titres of compounds of formula (I) or (IV) or downstream products.

In a further preferred embodiment the process of the invention includes contacting the compound of formula (II) or formula (III) with a β-lactam synthetase enzyme purified from the natural source, for example from *Streptomyces clavuligerus* in a cell-free environment. A process according to the invention for preparing an enzyme having β-lactam synthetase activity comprise the steps a) culturing *Streptomyces clavuligerus*,
b) harvesting and lysing the mycelium, and
c) isolating a polypeptide having at least 95% identity with the amino acid sequence of SEQ ID No.:2 over the entire length of SEQ ID No.:2 and having β-lactam synthetase activity.

A cell-free extract is produced, preferably by cation or other disruption of the microorganisms, optionally thereafter removing cell debris leaving the β-lactam synthetase enzyme in solution. This solution is then fractioned to isolate the β-lactam synthetase enzyme. The enzyme may be prepared by culturing the microorganism in a conventional manner, especially under aerobic conditions in a suitable liquid or semi-solid medium. In general, carbon and nitrogen sources which microorganisms can assimilate and inorganic salt nutrients essential for the growth of the microorganism are included in the culture medium.

The culture medium should contain a source of metal ions such as, for example, iron. The culture conditions may be a temperature in the range of from 10° C. to 80° C. and pH in the range of from 3 to 10. Preferred conditions are from 20° C. to 30° C. at a pH of from 5 to 9, suitably, for example, about pH 7, for 0.5 to 5 days.

The enzyme may be isolated and used in purified form, partially purified form, as obtained in an impure state, as a filtrate from a disrupted cell preparation, or as a crude cell homogenate. The enzyme can he recovered and purified from the disrupted cell preparation by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Most suitably the enzyme is, for example, at least partially purified to remove other enzymes which might catalyse the destruction of the precursor, the enzyme, or the clavam nucleus. The enzyme may be attached to an insoluble polymeric support.

The process of the present invention is generally carried out in aqueous media, the reaction mixture suitably being maintained in the range of from pH 4 to 9, more suitably, for example from 6.5 to 9.0, preferably about pH 8.5. The pH is suitably controlled, for example, using buffers, such as, for example, 3-(N-morpholino)propanesulphonic acid buffer at pH 7. Alternatively the pH may be controlled by the addition of a suitable acid or base. The temperature of the reaction should be that suitable for the enzyme employed and is generally in the range of from 15° C. to 60° C., preferably about 30° C. The reaction time depends on such factors as concentrations of reactants and cofactors, temperature and pH.

The compound of formula (II) or salt thereof is suitably dissolved, for example, in buffer before mixing with the enzyme. The concentration of precursor solution will depend upon the solubility of the precursor, usually the concentration of the precursor solution is in the range of from 5% w/v to 0.001% w/v. After the reaction is complete, the enzyme may be separated from the reaction mixture and the compound of formula (I), or a salt thereof, isolated by conventional methods. The initial purification of the compound of formula (I), or a salt thereof, conveniently involves a chromatography step. The compound of formula (I) may be isolated in a form where the carboxyl and/or the amino group present is protected and, if desired, the protecting group(s) may be subsequently removed to generate the compound in a pure form.

Salts of the compound of formula (I) may be produced, for example, by treating the unsalified compound with the appropriate acid or base. The compounds, and salts thereof, produced by the above processes, may be recovered by conventional methods.

Compounds of formula (I) possessing two chiral centres may be separated into diastereoisomeric pairs of enantiomers, if so desired, by, for example, fractional crystallisation from a suitable solvent, for example methanol or ethyl acetate or a mixture thereof. The pair of enantiomers or other pairs of enantiomers may be separated into individual stereoisomers by conventional means, for example by the use of an optically active salt as a resolving agent or by stereoselective removal of a protecting group using a suitable enzyme, for example an esterase such as subtilisin. In mixtures of diastereoisomers of the compounds the ratio of diastereoisomers may be changed by treatment with a non-nucleophilic base, for example 1,5-diazabicyclo[4.3.0]non-5ene.

Suitable optically active compounds which may be used as resolving agents are described in Topics in Stereochemistry, Vol. 6, Wiley Interscience, 1971, Allinger, N. L. and Eliel, W. L., Eds.

Alternatively, any enantiomer of a compound of formula (I) may be obtained by stereospecific synthesis using optically pure starting materials of formula (II) of known configuration.

Instead of employing a cell-free system, the process of this invention may also be operated using an intact host microorganism expressing the β-lactam synthetase enzyme through recombinant means, under conditions enabling conversion of the compound of formula (II) to the β-lactam compound of formula (I). The precursor compound of formula (II) or (III), or salt thereof, is provided and contacted with the microorganism to produce the compound of formula (I) or (IV) respectively, or salt thereof. The microorganism may be in the form of a growing culture, resting culture, washed mycelium, immobilised cells, or protoplasts.

In a further embodiment a cell-free system, derived from the recombinant organism, may be used to carry out the process of the invention. The cell-free extract may be prepared, and the enzyme purified, as hereinbefore described.

The β-lactam synthetase polypeptides useful in the present invention may be prepared by the use of β-lactam synthetase polynucleotides. Such polynucleotides include isolated polynucleotides comprising a nucleotide sequence encoding a polypeptide which has at least 95% identity to the amino acid sequence of SEQ ID NO:2, over the entire length of SEQ ID NO:2. In this regard, polypeptides which have 97–99% identity are highly preferred. Such polynucleotides include a polynucleotide comprising the nucleotide sequence contained in SEQ ID NO:1 encoding the polypeptide of SEQ ID NO:2.

The invention also provides the use of polynucleotides which are complementary to the above described polynucleotides.

Polynucleotides of the present invention may be obtained, using standard cloning and screening techniques from natural sources such as genomic DNA libraries, PCR from genomic DNA or can be synthesized using well known and commercially available techniques. Certain polynucleotides of the invention and the β-lactam synthetase polypeptides encoded by them are obtainable from *Streptomyces* species. In a preferred aspect the polynucleotides and polypeptides of the invention are obtainable from *Streptomyces clavuligerus*.

The polynucleotides used in the present invention may be DNA or alternatively RNA.

Recombinant polypeptides of the present invention may be prepared by processes well known in the art from recombinant host cells comprising recombinant expression vectors. A process of the invention for preparing an enzyme having β-lactam synthetase activity comprises the steps:

a) culturing a host microorganism transformed with a recombinant vector comprising a polynucleotide capable of producing the polypeptide having at least 95% identity with the amino acid sequence of SEQ ID NO:2 over the entire length of SEQ ID NO:2, and having β-lactam synthetase activity, and b) isolating the polypeptide as defined in (a).

In a further aspect, the present invention provides a recombinant vector comprising a polynucleotide capable of producing a β-lactam synthetase polypeptide when said recombinant vector is present in a compatable host. Compatable hosts include, but are not limited to, *E. coli* and *Streptomyces* species.

Cell-free translation systems can also be employed to produce such proteins using RNA polynucleotides.

Introduction of polynucleotides into host cells can be effected by methods described in many standard laboratory manuals, such as Davis et al, Basic Methods in Molecular Biology (1986) and Sam brook et al., Molecular Cloning: A Laboratory Manual, 2nd Ed., Cold Spring Harbor Laboratory Press, Cold Spring Harbor, N.Y. (1989).

A great variety of expression vectors can be used, for instance, chromosomal, episomal and virus-derived vectors, e.g., vectors derived from bacterial plasmids or from bacteriophages. The expression vectors may contain control regions that regulate as well as engender expression. Generally, any vector which is able to maintain, propagate or express a polynucleotide to produce a polypeptide in a host may be used. The appropriate nucleotide sequence may be inserted into an expression vector by any of a variety of well-known and routine techniques, such as, for example, those set forth in Sambrook et al., Molecular Cloning, A Laboratory Manual (supra). Appropriate secretion signals may be incorporated into the desired polypeptide to allow secretion of the translated protein into the periplasmic space or the extracellular environment. These signals may be endogenous to the polypeptide or they may be heterologous signals.

In a further aspect the host cell contains a high copy number of the β-lactam synthetase polynucleotide.

Culture of the recombinant host microorganism and isolation of the polypeptide are as described above.

The following definitions are provided to facilitate understanding of certain terms used frequently herein.

"β-lactam synthetase activity or β-lactam synthetase polypeptide activity" or "biological activity of the β-lactam synthetase or β-lactam synthetase polypeptide" refers to the enzyme activity which is capable of catalysing the conversion of compound (II) to (I), and in a preferred embodiment the conversion of compound (III) to (IV).

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

"% identity", as known in the art, is a measure of the relationship between two polypeptide sequences or two polynucleotide sequences, as determined by comparing their sequences. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology.

Methods for comparing the identity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis. USA), for example the programs BESTFIT and GAP, may be used to determine the % identity between two polynucleotides or two polypeptide sequences. BESTFIT uses the "local homology" algorithm of Smith and Waterman (Advances in Applied Mathematics, 2, 482–489, 1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443–453, 1970). GAP is more suited to comparing sequences which are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities are determined when the two sequences being compared are optimally aligned.

Other programs for determining identity between sequences are also known in the art, for instance the BLAST family of programs (Altschul S F et al, J Mol Biol, 215, 403–410, 1990, Altschul S F et al, Nucleic Acids Res., 25:389–3402, 1997, available from the National Center for Biotechnology Information (NCBI), Bethesda, Maryland, USA and accessible through the home page of the NCBI at www.ncbi.nlm.nih.gov) and FASTA (Pearson W R and Lipman D J, Proc Nat Acad Sci USA, 85, 2444–2448, 1988, available as part of the Wisconsin Sequence Analysis Package). Preferably, the BLOSUM62 amino acid substitution matrix (Henikoff S and Henikoff J G, Proc. Nat. Acad Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value.

EXAMPLES

All general procedures and recipes for buffers and media were carried out as described in "Molecular Cloning:- A Laboratory Manual", Sambrook, Fritsch and Maniatis, 2nd edition, Cold Spring Harbour laboratory Press (1989).

1) Construction of the Vector pBLS1

1.1 Preparation of Digested Vector:

DNA of the plasmid vector pYZ4 (Zhang & Broome-Smith Gene 1996 p51–57, 1990) was prepared from an *E. coli* culture using standard plasmid miniprep techniques. To 9 μl of this miniprep sample was added 1.5 μl of EcoRI, 1.5μl KpnI, 1.5 μl×10 reaction buffer supplied by the manufacturer and 1.5 μl H$_2$O and the sample digested for 2 hours at 37° C. The enzymes were extracted with phenol/chloroform and the DNA isolated by ethanol precipitation. The DNA pellet was resuspended in 4 μl TE.

1.2. Preparation of the 4.1 kb EcoRI/KpnI DNA Fragment Containing orf3:

DNA of a cosmid containing the 11.6 kb EcoR1 fragment described in Canadian patent application no. 2108113 was prepared from an *E. coli* culture using standard miniprep techniques. To 9 μl of this miniprep sample was added 1.5 μl of EcoRI, 1.5 μl KpnI, 1.5 μl×10 reaction buffer and 1.5 μl H$_2$O and the sample digested for 2 hours at 37° C. The enzymes were extracted with phenol/chloroform and the DNA isolated by ethanol precipitation. The pellet was resuspended in 4 μl TE.

1.3. Ligation:

The 4 μl sample of the 4.1 kb DNA fragment from example (1.2) was mixed with 4 μl of digested vector from example (1.1). To this was added 1 μl of ×10 ligase buffer and 1 μl of T4 ligase. Following incubation overnight at 4° C., 2.5 μl of the solution was used to transform 80 μl of *E. coli* XL1-Blue competent cells (Stratagene), plated onto LB agar plates (+kanamycin) and incubated overnight at 37° C. Miniprep DNA isolation and subsequent restriction digest analysis (BamHI/BglII, HindIII/SacI, HindIII/SphI, SalI, BamHI/NotI) of several of the kanamycin resistant transformants confirmed that a plasmid had been obtained containing the 4.1 kb EcoRI/KpnI fragment containing orfs2 and 3 of the clavulanic acid gene cluster. This plasmid was named pBLS1.

2) Construction of the Vector pBLS2

2.1. Preparation of Digested Vector:

A 1.5 µl sample of the pET-24d(+) expression vector (Novagen) was diluted with 9 µl with $H_2O$. To this was added 1.5 µl of BamHI, 1.5 µl of ×10 restriction buffer and 3.0 µl $H_2O$ and the sample was incubated for 2 hours at 37° C. The restricted vector was then dephosphorylated by treating with I U calf alkaline intestinal phosphatase (New England Biolabs), at 37° C. for 1 hr. The mixture was analysed by agarose gel and a DNA fragment of 5.4 Kb was isolated, finally eluting into 20 µl $H_2O$.

2.2. Preparation of the Insert Fragment:

50 µl sample of pBLS1 vector DNA from example (1.3) was isolated from the dam *E. coli* strain GM2163 (New England Biolabs). The use of this strain was essential to facilitate cleavage of the DNA by the restriction enzyme BclI. To 9 µl of this was added 1.5 µl BclI, 1.5 µl of ×10 BclI buffer, and 3.0 µl $H_2O$ before incubating at 37° C. for 1 hr. The mixture was analysed by agarose gel and a DNA fragment of 2 kb isolated and eluted in 10 ml $H_2O$.

2.3. Ligation:

A 6.5 µl sample of DNA prepared from example (2.2) was mixed with 1 µl of DNA prepared from example (2.1). To this were added 1 µl of ×10 ligase buffer, 0.5 µl ATP (1 mM) and 1 µl of T4 ligase. The mixture was incubated at 16° C., for 16 hours and 2.5 µl of the solution was used to transform 40 µl of XL1 -Blue competent cells ( Stratagene) before being plated onto LB agar plates (+kanamycin) and incubated overnight. Ten kanamycin resistant colonies were picked at random, grown up and the plasmid DNA isolated by miniprep. Restriction digest with SalI indicated that one clone contained the 2 kb BclI DNA fragment as required. This clone was analysed by further restriction digests (SmaI, Bgl II, NcoI and SalI) which generated the expected fragmentation patterns confirming that orf3 had been cloned. This plasmid was named pBLS2.

3) PCR of orf3 Fragment from pBLS2

PCR amplification of the targeted gene was carried out using standard PCR techniques, pBLS2 miniprep DNA from example (2.3) was used as template DNA. Primers were used at a concentration of 10 µM in TE. The 10× ThermoPol reaction buffer used contained 200 mM Tris-Cl (pH 8.8), 20 mM $MgSO_4$, 100 mM KCl, 100 mM $(NH_4)_2SO_4$, 1% Triton X-100. dNTP solutions were used at a concentration of 100 nM.

Because the pET24a expression vector was used, the 5' primer incorporated an Nde1 site in frame with the start codon and the 3' primer a BamHI site as shown below:

5' primer:

(SEQ ID NO:3)

NdE1
5' G GAA TCC CAT ATG GGG GCA CCG GTT CTT C 3'

3' primer:

(SEQ ID NO:4)

BamH I
5' CGC GGA TTC CTA GGC CGC CCC CCG CG 3'

The underlined portions of the primer sequences denotes coding region.

The following reaction components were all added and the mixture heated to 96° C. for 4 minutes before the DNA polymerase was added. The reaction mixture was overlaid with 100 µl mineral oil before the reaction was continued.

The optimised reaction mixture contained the following:

| | |
|---|---|
| $H_2O$ | 50.5 µl |
| DMSO (50%) | 20 µl |
| Buffer | 10 µl |
| $MgSO_4$ | 2.5 µl |
| dNTPs | 4 × 1 µl |
| 5' Primer | 1 µl |
| 3' Primer | 1 µl |
| DNA Template | 10 µl |
| Vent DNA polymerase (New England Biolabs) | 1 µl. |

Temperature profile:

1. 96° C. 4 min then add enzyme and mineral oil
2. 95° C. 4 min
3. 60° C., 1.5 min
4. 72° C. 2 min
5. 95° C. 1 min
6. 60° C., 1.5 min
7. 72° C. 2 min
8. 25 cycles of steps 5 to 7
9. 95° C. 1 min
10. 60° C. 1.5 min
11. 72° C. 10 min
12. 4° C. incubate The expected PCR product (1.5 kb) was isolated from agarose gel and eluted into 30 µl TE.

4) Construction of the Vector pBLS3

4.1. Preparation of Digested Vector:

A 45 µl sample of the pET-24a(+) expression vector (Novagen) isolated by DNA miniprep was digested using 4 µl BamHI, 4 µl NdeI and 6 µl of ×10 reaction buffer. The mixture was incubated at 37° C. for 18 hrs and 5 µl was analysed by agarose gel electrophoresis. The DNA fragment at 5.4 kb was isolated and eluted into 5 µl of TE.

4.2. Preparation of the Insert Fragment:

30 µl of the orf3 PCR product from example (3) were digested with 3 µl BamHI, 3 µl NdeI, with 4 µl of ×10 reaction buffer. The mixture was incubated at 37° C. for 18 hrs and all of the mixture analysed by agarose gel electrophoresis. A DNA fragment corresponding to a size of 1.5 kb was isolated, and eluted in 5 µl $H_2O$.

4.3. Ligation:

1.0 µl sample of DNA from example (4.2) was mixed with 3.0 µl of DNA from example (4.1). To this was added 1 µl of ×10 ligase buffer, 1.0 µl ATP(1 mM), 1.0 µl of T4 ligase and 3.0 µl of $H_2O$. The mixture was incubated at 23° C. for 2 hours then at 16° C., for 16 hours. The mixture (5µl) was transformed into 100 µl XL1 -Blue before being plated onto LB agar plates (+kanamycin) and incubated overnight at 37° C. Miniprep DNA isolation and subsequent restriction digest analysis of several of the kanamycin resistant transformants confirmed that the expected plasmid had been obtained containing the 1.5 kb PCR generated fragment containing orf3. As further confirmation, the DNA sequence of the cloned PCR product was confirmed. This plasmid was named pBLS3.

5) Isolation of Protein from *E. coli* Fermentations

A 50 µl sample of pBLS3 vector DNA from example (4) was isolated from a 1.5ml culture of XL1- Blue(pBLS3). To 100 µl of *E. coli* BL21(DE3) competent cells (New England Biolabs) were added 5 µl of this mini prep DNA. The cells were then used to inoculate LB agar plate (+kanamycin) and the plates were incubated overnight at 37° C.

5.1 Small Scale:

A single colony of *E. coli* BL21(DE3) containing pBLS3 was used to inoculate 5 ml of LB containing Kanamycin. This was grown at 37° C. for 4 hours, then 2ml were used to inoculate 100 mls is of 2YT (+kanamycin) and left to grow for another 2 hours at 37° C. The cultures were then induced with IPTG to a level of 0.1 mM, and left to grow at 37° C. overnight(17 hours) before being harvested by centrifugation at 4° C. and stored at −20° C.

5.2. Large Scale:

Larger scale fermentation was achieved by using a single colony of *E. coli* BL21(DE3) containing pBLS3 to inoculate 200 ml 2YT which was grown overnight at 37° C. 10 ml of this was used to inoculate 500 ml of 2YT and grown for 5 hours before being induced to a level of 0.1 mM IPTG and left to grow for a further 4 hours before being harvested as before.

6) Purification of the orf3 Protein 6.1 Sample Preparation:

The volumes of the buffers used were scaled according to the weight of cells to be processed. Typically 30g of cells (prepared as described in example (5)) were resuspended in 90 ml Lysis buffer; 50 mM Tris-HCl (pH8), 100 mM NaCl, 10% glycerol, 2 mM DTT, 3 mM EDTA. Then lysozyme was added to produce a final concentration of 0.5 mg/ml and the mixture stirred for 20 minutes at 4° C. The cells were then lysed using a sonicator (5×10 seconds). 15 mM $MgCl_2$ and 20 µg/ml DNaseI were then added and the mixture stirred for another 15 minutes at 4° C. The mixture was then centrifuged for 30 minutes at 20,000 rpm at 4° C. The supernatant was removed and 0.05% polyethylimine and 1% streptomycin added. The mixture was then stirred for 20 minutes at 40° C. to precipitate out the DNA which was removed by centrifugation at 20,000 rpm at 4° C. for 25 minutes. The supernatant was filtered before being mixed with 150 ml of buffer (buffer A for FPLC described in example 6.2) ready for loading onto the FPLC system.

6.2 FPLC Set-Up:

FPLC was carried out on a Pharmacia LCC-500 plus gradient controller with a P-500 pump and Pharmacia FRAC-200 rotary fraction collector. Elution of proteins was monitored by U.V. absorption at 280 nm.

ColumnQ Sepharose, 100 ml
Buffer A 25 mM Tris-HCl(pH 8.), 2 mM DTT, 1 mM EDTA
Buffer B 25 mM Tris-HCl(pH8.0), 2 mM DTT, 1 mM EDTA, 2M NaCl
Gradient 0–8% B over 50 ml at 8 ml/min
8–18% B over 500 ml at 8 ml/min
Fractions 10 ml fractions collected Using this system 50×10 ml fractions were collected. Analysis by SDS-PAGE gel indicated that the fractions containing orf 3 were 13 to 23. This was confirmed by further analysis of these extracts by Western blot analysis using an anti-orf3 polyclonal antibody raised against a 16 amino acid peptide corresponding to a region close to the C-terminus of the predicted orf3 protein (VGGGRHPSEVDTDDVC) (SEQ ID NO:5) (Canadian patent application no. 2108113) which gave a positive result for the 56 KDa protein corresponding to the predicted size of the orf3 protein.

From SDS-PAGE gel anaylsis of the protein fractions collected by this method it was estimated that the best fractions containing orf3 were ca. 40% pure.

As a final confirmation of the orf3 protein N-terminal amino acid sequencing was undertaken using standard Edman degradation methodology. The sequence generated from this showed 100% sequence identity with the predicted sequence (FIG. 12 in Canadian patent application no. 2108113), ie.

$NH_2$-GAPVLPAAFGFLASARTGGG (SEQ ID NO:6)

7) Assays for Functionality of orf3 protein

The crude extracts prepared from the recombinant *E. coli* containing the pBLS3vector (example 5) and the purified protein product (example 6) were tested for the ability to catalyse the conversion of the compound (III) to compound (IV). Both compound (III) and compound (IV) were prepared synthetically following previously published methods (Baldwin et al J. Chem Soc. Chem Comm. 1993 p500–2 and Elson et al J. Chem Soc. Chem Comm. 1993 p1212–4).

7.1

Protein extracts were assayed for the conversion of compound (III) to compound (IV) under the following conditions:

| Assay mix | Enzyme* (ca. 3 mg/mL) | 150 ml |
|---|---|---|
| | Compound (III) (1M) | 10 ml |
| | MOPS (1M, pH 7.4) | 20 ml |
| | $Mg(AcO)_2$ (1M) | 5 ml |
| | ATP (0.5M) | 5 ml |

*negative controls were: 150 ml extract fractions containing no orf3 protein or 150 ml water.

The above mixture was heated at 37 ° C. for 15 minutes before being analysed by the HPLC methods described below.

7.2 Underivitised HPLC Assay Conditions.

This assay was carried out using the following equipment and conditions
Waters 746 data module
Waters 600E system controller
Waters 712 WISP injector
Waters 848 tunable absorbance detector

| Program | Time | Flow (ml/min) | A | B |
|---|---|---|---|---|
| | 0 | 0.8 | 100 | 0 |
| | 25 | 0.8 | 0 | 100 |
| | 34 | 0.8 | 0 | 100 |
| | 35 | 0.8 | 100 | 0 |

When extracts were used in this assay which had been shown to contain the orf3 protein (as described in example (6)) a peak was seen at 10.94 mins on the HPLC trace which correlated with the retention time for compound (IV). This peak was not detected if compound (III), ATP or the orf3 containing protein extract was omitted from the assay. The peak could also not be detected if other protein extracts, which did not contain the orf3 protein, were collected from the FPLC and assayed by the same method.

The peak identified at 10.94 mins was manually collected and submitted for electrospray mass spectrometry analysis where it was shown to have a molecular weight of 229, which is the positive ion equivalent of compound (IV). For final confirmation that this peak corresponded to compound (IV) several samples of the peak were combined, freeze dried and submitted for 500 MHz nmr analysis. The spectrum produced in this test was consistent with the product of the reaction being compound (IV).

7.3 Benzoin Derivatised HPLC Assay Conditions:

The protocol used was Kai et al. (M. Kai, T. Miyazaki, M. Yamaguchi, Y Ohkura, J. Chromatog. 268, 417–424, 1983) which assays for compounds containing guanidino functionalities using a fluorescence detector. The following equipment and conditions were used:

Waters 746 data module
Waters 600E system controller
Waters 712 WISP injector
Waters 848 tunable absorbance detector
Jasco FP-920 intelligent fluorescence detector
Column Phenyl 250×4.6 mm
Buffer A Methanol: Water: 0.5 M Tris-HCl(pH8.5) 50:35:15
Buffer B Methanol: Water: 0.5 M Tris-HCl(pH8.5) 80:5:15

| | |
|---|---|
| Column | ODS, 250 mm × 1 mM |
| Mobile phase | H$_2$O |
| Flow rate | 4 ml/min |
| Detection | 218 nm |
| Sample injected | 200 ul |

Reagents Benzoin solution (4.0 mM)
   b-Mercaptoethanol (0.1 M)-sodium sulphite (0.2 M) solution
   Sodium hydroxide (2.0 M)
   Tris-HCl (0.5 M, pH 9.2)-Hydrochloric acid (2 M)
Method To a 200 μl sample of the incubated assay mixture described in example (7.1) was added 100 μl of benzoin solution and 100 μl μ-mercaptoethanol solution. Then whilst on ice 200 μl of NaOH was added. The mixture was then heated on a hot block at 100° C. for 5 minutes and returned to ice. Whilst on ice 200 μl of Tris-HCl solution was added. 200 μl of this sample were then injected onto the column.

A portion of the collected fraction from the HPLC purified reaction mixture described in example (7.2) was derivatised with benzoin. This sample showed a retention time that matched with that of compound (IV). The crude reaction mixture was also derivatised with benzoin and this gave peaks correlating to unused compound (III) and the product compound (IV).

As found with the results from the underivitised HPLC experiment from example (7.2), a peak corresponding to compound (IV) was only detected when the orf3 protein was present in the assay and not when compound (III), ATP or the orf3 containing protein extract was omitted. Also a peak corresponding to compound (IV) could not be detected if other protein extracts which did not contain the orf3 protein were collected from the FPLC were assayed by the same method.

These results demonstrate that the orf3 product catalysis the conversion of compound (III) to compound (IV). To reflect the fact that this reaction produces a monocyclic β-lactam the enzyme was named β-lactam synthetase 1 (BLS 1).

Abbreviations
TE Tris EDTA buffer (Sambrook et al supra)
YT Yeast Tryptone broth/agar (Sambrook et al supra)
IPTG Isopropyl β-D-thiogalactopyranoside
DTT Dithiothreitol
EDTA Ethylenediaminetetraacetic acid
HPLC High Performance Liquid Chromatography
FPLC Fast Protein Liquid Chromatography Sequence information.
SEQ ID NO:1
ATGGGGGCACCGGTTCTTCCGGCTGCCT-
TCGGGTTCCTGGCCTCCGC-
CCGAACGGGCGGGGGCCGGGCCCCCG GCCCG-
GTCTTCGCGACCCGGGGCAGCCACACCGACAT
CGACACGCCCCAGGGG-
GAGCGCTCGCTCGCGGCGAC CCTGGTGCACGC-
CCCCTCGGTCGCGCCCGACCGCGCGGTG-
GCGCGCTCCCTCACCGGCGCGCCCACCACCGCG
GTGCTCGCCGGTGAGATCTACAACCGG-
GACGAACTCCTCTCCGTGCTGCCCGCCG-
GACCCGCGCCGGAGGGGG ACGCGGAGCTGGTC-
CTGCGGCTGCTGGAACGCTATGACCTGCATGCC
TTCCGGCTGGTGAACGGGCGCTTCGC GAC-
CGTGGTGCGGACCGGGGACCGGGTCCT-
GCTCGCCACCGACCACGCCGGTTCGGGT-
GCCGCTGTACACCTG
TGTGGCGCCGGGCGAGGTCCGGGCGTC-
CACCGAGGCCAAGGCGCGCTCGCCGCG-
CACCGCGACCCGAAGGGCT TCCCGCTCGCG-
GACGCCCGCCGGGTCGCCGGTCTGACCGGTGT
CTACCAGGTGCCCGCGGGCGCCGTGATGGA
CATCGACCTCGGCTCGGGCACCGCCGT-
CACCCACCGCACCTGGACCCCGGGC-
CTCTCCCGCCGCATCCTGCCG GAGGGCGAGGC-
CGTCGCGGCCGTGCGGGCCGCGCTGGAGAAGG
CCGTCGCCCAGCGGGTCACCCCCGGCGACA
CCCCGTTGGTGGTGCTCTCCGGCG-
GAATCGACTCCTCCGGGGTCGCGGCCT-
GTGCGCACCGGGCGGCCGGGGA ACTGGACACG-
GTGTCCATGGGCACCGACACGTCCAACGAGTT
CCGCGAGGCCCGGCGGTCGTCGACCATCTG
CGCACCCGGCACCGGGAGATCAC-
CATCICCGACCACCGAGCTGCTGGCG-
CAGCTCCCGTACGCGGTGTGGGCC TCCGAGTCG-
GTGGACICCGGACATCATCGAGTACCTGCTCCC
CCTGACAGCGCTCTACCGGGCGCTCGACGGG
CCGGAGCGCCGCATCCTCACCGGGTACG-
GCGCGGACATCCCCCTCGGGGGCATG-
CACCGCGAGGACCGGCTGC CCGCGCTGGACAC-
CGTTCTCGCGCACGACATGGCCACCTTCGACGG
GCTGAACGAGATGTCCCCGGTGCTGTC
CACGCTGGCGGGGCACTGGACCACCCAC-
CCGTACTGGGACCGGGAGGTCCTC-
GATCTGCTGGTCTCGCTGGAG GCCGGGCT-
CAAGCGGCGGCACGGC
SEQ ID NO:2
GAPVLPAAFGFLLSARGGGRAPGPV-
FATRGSHDIDTPOGERSLAATLVHAPS-
VAPDRAVARSLTGTATTAVPP LACEIYNRDELLSV-
LPAGPAPEODAELVLfiLLERYDLMAFRLVVGRFA
TVVRTGDRVLLATDHAGSVPLYTV CIVAPGEV-
RASTEAAAHDPKrjFPLADARRVAGLT-
GVYQVPAGAVMDIOLGSGTAVrXRTWT-
PGLSRRILPEG
ADSEAVAARAEKAVAORVPGDPLVVLSG-
GIISSGVAACARRAACELDTVSMCT-
DTSNFRARVVDHLRTIIPRD RKREITIMTTEL-
LAQLPYAVWASESVDPDIIEYLLPLTkLYRALDrPE
RRILTGYGADIPLGGMHREDRLPAL DVLAHDKAT-
FDGLNEMSPVLSTLAGHWTTHPYWDREV-
LLLVSLFAGLKRRHGRDKWVLRAMPA-
ETVVHGTRSV
NRPKLCVHEGSCTTSSFSRLLLDHGVAE-
ORVHEAKRQVVRELFCLrVGGGRHPSM-
VTDDVVRSVADRTARGAT

What is claimed is:

1. A process for preparing compounds of formula (I)

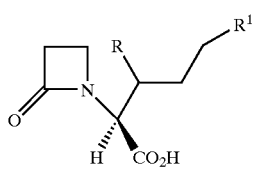

(I)

wherein R is H or OH and $R^1$ is

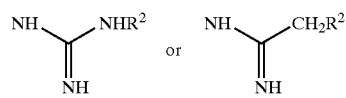

and where $R^2$=H or $C_{1-6}$ alkyl comprising the steps of:

a) culturing a host cell comprising a vector comprising an isolated polynucleotide encoding a polypeptide comprising a sequence having at least 95% identity to the amino acid sequence of SEQ ID NO:2 over the entire length of SEQ ID NO:2 and having β-lactam synthetase activity;
b) harvesting said host cell;
c) at least partially purifying said polypeptide;
d) contacting said at least partially purified polypeptide with a compound of formula (II)

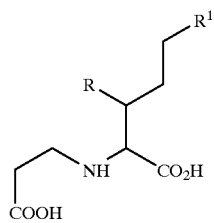

where the variables are as defined in formula (I).

2. The process of claim 1, wherein said isolated polynucleotide comprises SEQ ID NO: 1.

3. The process of claim 1, wherein said polypeptide is at least partially purified by a method selected from the group consisting of: ammonium sulfate precipitation, ethanol precipitation, acid extraction, anion exchange chromatography, cation exchange chromatography, phosphocellulose chromatography, hydrophobic interaction chromatography, affinity chromatography, hydroxylapatite chromatography and lectin chromatography.

4. A process for preparing a compound of formula (IV)

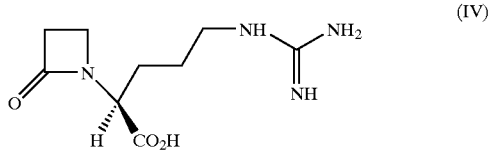

comprising the steps of:

a) culturing a host cell comprising a vector comprising an isolated polynucleotide encoding a polypeptide comprising a sequence having at least 95% identity to the amino acid sequence of SEQ ID NO:2 over the entire length of SEQ ID NO:2 and having β-lactam synthetase activity;
b) harvesting said host cell;
c) at least partially purifying said polypeptide; and
d) contacting said at least partially purified polypeptide with $N^2$-(2-carboxyethyl)-(S)-arginine; formula (III).

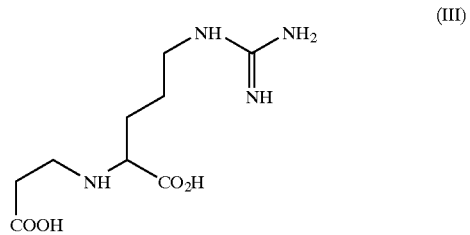

5. The process of claim 4, wherein said isolated polynucleotide comprises SEQ ID NO: 1.

6. The process of claim 4, wherein said polypeptide is at least partially purified by a method selected from the group consisting of: ammonium sulfate precipitation, ethanol precipitation, acid extraction, anion exchange chromatography, cation exchange chromatography, phosphocellulose chromatography, hydrophobic interaction chromatography, affinity chromatography, hydroxylapatite chromatography and lectin chromatography.

7. A process according to claim 1 or 4 wherein the polypeptide comprises the amino acid sequence of SEQ ID NO:2.

8. A process according to claim 1 or 4 wherein the polypeptide consists of the amino acid sequence of SEQ ID NO:2.

* * * * *